US006647092B2

(12) United States Patent

Eberhard et al.

(10) Patent No.: US 6,647,092 B2
(45) Date of Patent: Nov. 11, 2003

(54) RADIATION IMAGING SYSTEM AND METHOD OF COLLIMATION

(75) Inventors: Jeffrey Wayne Eberhard, Albany, NY (US); Reinhold Franz Wirth, Ballston Spa, NY (US); Bernhard Erich Hermann Claus, Niskayuna, NY (US); Ralph Allen Hewes, Burnt Hills, NY (US); Harold John Jenkins, Jr., Amsterdam, NY (US)

(73) Assignee: General Electric Company, Niskayuna, NY (US)

( * ) Notice: Subject to any disclaimer, the term of this patent is extended or adjusted under 35 U.S.C. 154(b) by 0 days.

(21) Appl. No.: 09/683,564

(22) Filed: Jan. 18, 2002

(65) Prior Publication Data

US 2003/0138078 A1 Jul. 24, 2003

(51) Int. Cl.7 .................................................. A61N 5/10
(52) U.S. Cl. ......................................... 378/65; 378/150
(58) Field of Search .......................... 378/65, 145, 146, 378/147, 148, 150, 151, 152, 153

(56) References Cited

U.S. PATENT DOCUMENTS

| | | | | |
|---|---|---|---|---|
| 5,231,654 A | | 7/1993 | Kwasnick et al. | 378/147 |
| 5,231,655 A | | 7/1993 | Wei et al. | 378/147 |
| 5,293,417 A | | 3/1994 | Wei et al. | 378/147 |
| 5,303,282 A | | 4/1994 | Kwasnick et al. | 378/147 |
| 5,369,678 A | * | 11/1994 | Chiu et al. | 378/62 |
| 5,430,298 A | | 7/1995 | Possin et al. | 250/370.11 |
| 6,055,295 A | * | 4/2000 | Murthy et al. | 378/151 |
| 6,173,033 B1 | * | 1/2001 | Klingenbeck-Regn et al. | 378/20 |
| 6,173,039 B1 | | 1/2001 | Hampel et al. | 378/150 |
| 6,260,999 B1 | * | 7/2001 | Wofford et al. | 378/205 |
| 6,322,249 B1 | * | 11/2001 | Wofford et al. | 378/207 |
| 6,389,108 B1 | * | 5/2002 | Ein-Gal | 378/147 |

* cited by examiner

*Primary Examiner*—Drew A. Dunn
*Assistant Examiner*—Allen C. Ho
(74) *Attorney, Agent, or Firm*—Ann M. Agosti; Patrick K. Patnode

(57) ABSTRACT

A radiation imaging system comprises a movable radiation source adapted to be disposed in a plurality of respective radiation source positions; a radiation detector and a collimator assembly configured to displace a collimator in a plurality of respective collimator positions, each of the collimator positions being coordinated with at least one of the radiation source positions such that a radiation beam emanating from the radiation source is collimated to limit radiation incident on the detector to a predetermined exposure area. Another radiation imaging system comprises a movable radiation source; a radiation detector; and a collimator comprising an adjustable geometry aperture assembly configured such that an adjustment of the aperture geometry is synchronized with the movement of the radiation source and coordinated with the radiation source position so as to limit the incident radiation to a predetermined exposure area at the detector.

35 Claims, 9 Drawing Sheets

RADIATION IMAGING SYSTEM AND METHOD OF COLLIMATION

FEDERAL RESEARCH STATEMENT

The invention was made with Government support under contract number DAMD17988109 awarded by the U.S. Army. The Government has certain rights in the invention.

BACKGROUND OF INVENTION

The present invention relates generally to X ray radiation imaging systems and more particularly to a method and apparatus for collimating X rays to avoid excess dosage to the patient.

Collimators are used in applications where it is desirable to permit only beams of radiation emanating from the radiation source in a particular direction to pass beyond a selected path or a plane. In radiation imagers, collimators are used to ensure that no radiation beams emanating along a direct path from the radiation source miss the detector and hit unintended parts of the object. Collimators are positioned to substantially absorb the undesired radiation. Collimators are traditionally made of a material that has a relatively high atomic number. Collimator design affects the field of view of the imaging system. With the introduction of new imaging applications, the conventional collimators have a disadvantage that excess X rays can spill past the edge of the detector surface (or other predetermined exposure area), or that not the entire detector surface (or other predetermined exposure area) is exposed to incident X rays.

In the conventional imaging systems, collimators are used for standard examinations. One such configuration of a collimator comprises an X ray opaque metal with a simple aperture. In another collimator embodiment the aperture is formed by blades that are motor driven to fixed opening sizes. During the course of an X ray exam, typical in tomosynthesis, stereotaxy, stereo imaging and mammography where the X ray source travels in a prescribed arc (or other prescribed trajectory) around the object (patient), it is important to prevent any unnecessary X ray dose to reach the object. Presently the limitation of radiation exposure to the object is governed by US regulation CDRH 21 CFR 1020.30 (k).

In such advanced imaging systems, it is desirable to minimize the radiation exposure to the patient, minimize the complexity of the collimator in terms of its mechanical, electrical and software implementation, assure high speed of response of the system so that multiple images can be acquired in rapid succession, control the movement of the collimator with respect to other motion in the imaging system, and assure maximum field of view at the detector consistent with system constraints.

SUMMARY OF INVENTION

Briefly, in accordance with one embodiment of the invertion, a. radiation imaging system comprises a movable radiation source adapted to be disposed in a plurality of respective radiation source positions, a radiation detector and a collimator assembly. The collimator assembly comprises a collimator and a collimator positioning apparatus which is configured to displace the collimator in a plurality of respective collimator positions. Further, each of the collimator positions is coordinated with at least one of the radiation source positions such that a radiation beam emanating from the radiation source is collimated to limit radiation to a predetermined exposure area on the detector.

In accordance with another embodiment of the present invention, a method for radiation imaging comprises positioning a radiation source in a plurality of respective radiation source positions; displacing a collimator in a plurality of respective collimator positions where each of the collimator positions corresponds to a respective one of the radiation source positions such that a radiation beam emanating from the radiation source is collimated to limit the incident radiation to a predetermined exposure area on the detector; and detecting the radiation beam on the radiation detector.

In accordance with another embodiment of the present invention, a radiation imaging system comprises a movable radiation source, a radiation detector and a collimator comprising an adjustable geometry aperture assembly configured such that an adjustment of the aperture geometry is synchronized with the movement of the radiation source and coordinated with the radiation source position so as to limit the incident radiation to a predetermined exposure area at the detector.

In accordance with another embodiment of the present invention, a method for radiation imaging, comprises moving a radiation source in a plurality of radiation source positions; adjusting an aperture by synchronizing the aperture geometry adjustment with the movement of the radiation source and coordinating at least one of the position and the shape of the aperture with the respective position of the radiation source such that a radiation beam emanating from the radiation source is collimated to limit the incident radiation to a predetermined exposure area; and detecting the radiation beam on a radiation detector.

BRIEF DESCRIPTION OF DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
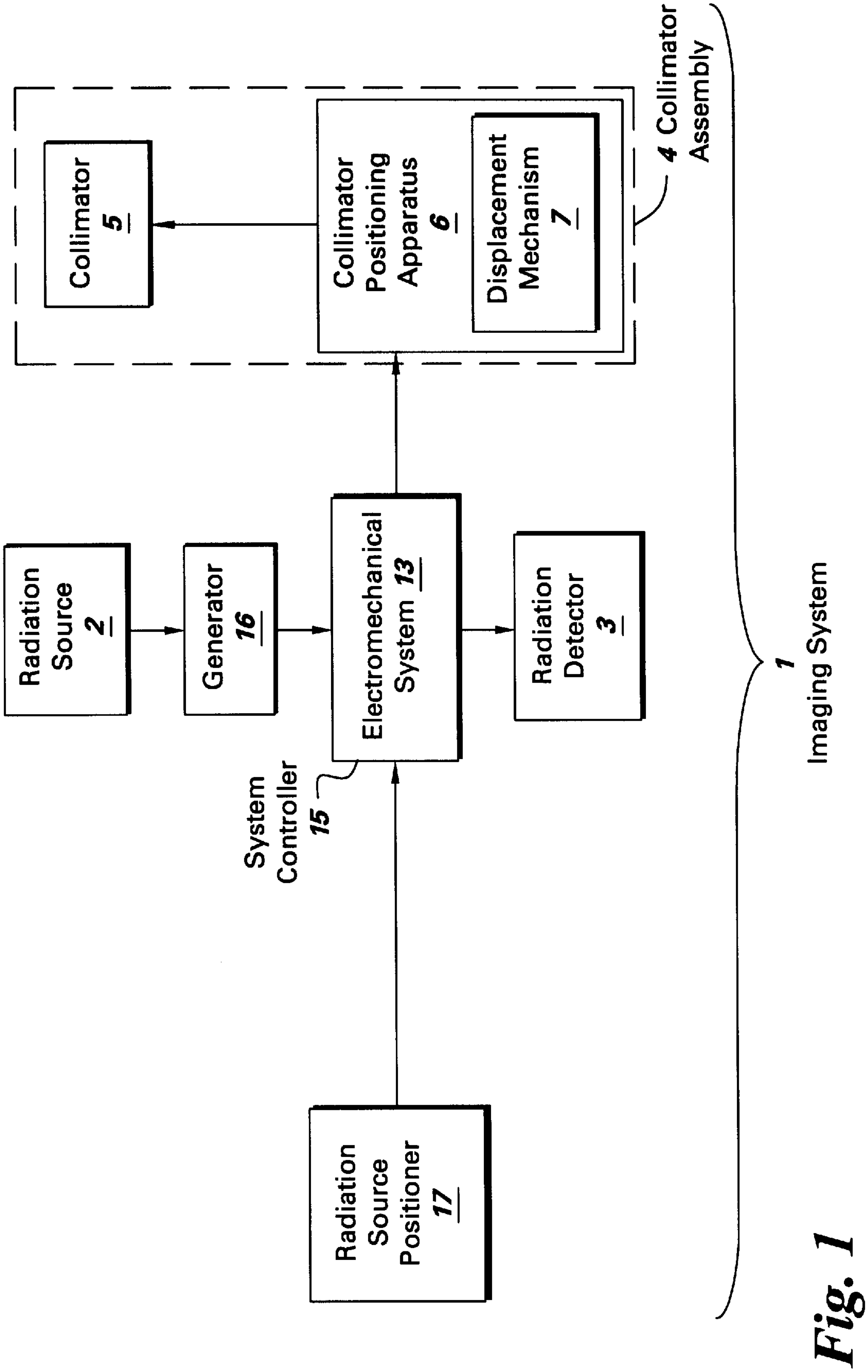
FIG. 1 illustrates a system block diagram of an imaging system according to one embodiment of the present invention.
Figure 2:
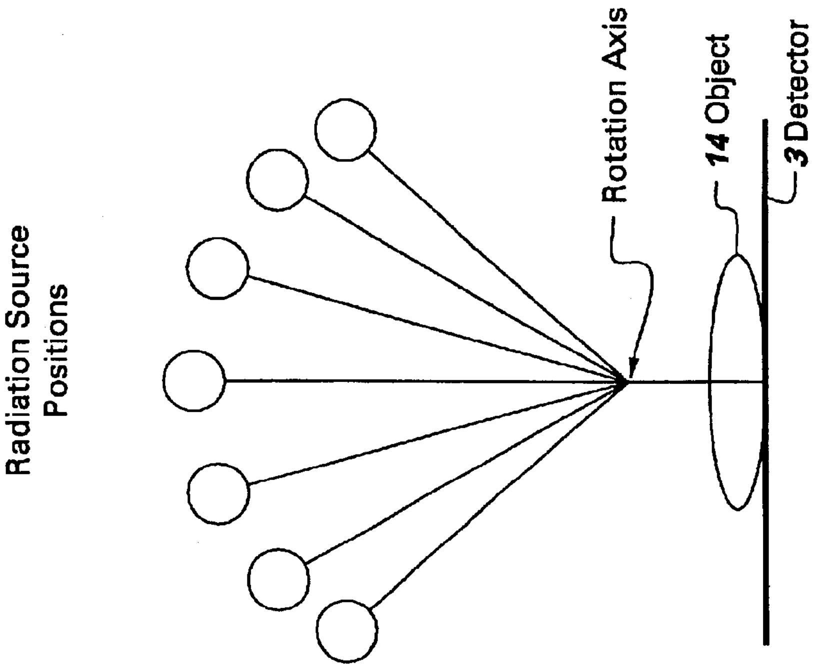
FIG. 2 illustrates a plurality of radiation source positions according to one embodiment of the present invention.

One embodiment of the present invention is a radiation imaging system 1, as illustrated in FIG. 1, comprising a movable radiation source 2, a radiation detector 3, and a collimator assembly 4. As the radiation source moves relative to an object 14, it assumes a plurality of radiation source positions resulting in the radiation beam emanating from the radiation source intersecting the object at various angles, as shown in FIG. 2. The collimator assembly 4, which is typically in a fixed spatial relationship to the X ray source has flexibility to be configured to position the collimator to limit the radiation incident on the detector to a predetermined exposure area. The predetermined exposure area typically comprises a region of interest for a particular imaging task, an active area of the detector, or the area of the X ray image receptor. The radiation source is configured to be displaced in a plurality of radiation source positions with respect to the object 14, by a radiation source positioner 17, fed by a generator 16 and a system controller 15, comprising an electromechanical system 13 and embedded software. "Movable radiation source" means that the source is free to travel in any direction typical in tomosynthesis and related applications. Non-limiting examples of imaging systems wherein embodiments of the present invention are particularly useful include tomosynthesis, stereotaxy, stereo imaging, for example in mammographic imaging systems.

FIG. 1 also illustrates the collimator assembly 4 according to one embodiment, which includes a collimator 5, and a collimator positioning apparatus 6. The collimator positioning apparatus is configured to displace the collimator to have a plurality of collimator positions such that each collimator position is coordinated with at least one of the radiation source positions. The collimator positioning apparatus is configured to provide movement to the collimator so that each of the collimator positions relates to at least one specific radiation source position at any given time during the imaging process. Further, the movement of the collimator and the radiation source are synchronized such that movement of the collimator occurs in the same time interval as the movement of the radiation source, and both are moving in a coordinated fashion.

In one embodiment, the movement of the collimator is also controlled so that each collimator position corresponds to a specific spatial relationship with radiation source and detector. Spatial relationship is defined as the relationship of the collimator position with the position of the radiation source and the radiation detector in the three dimensional space containing the source, collimator and detector. This coordination of the collimator position with the positions of the radiation source and the detector results in collimating and limiting the radiation beam from the radiation source to a predetermined exposure area on the detector and thus avoiding exposure of the object 14 to x-rays that do not contribute to the image formed at the detector. Spillage is defined as X rays emanating from the radiation source, which pass through the collimator aperture along a direct path from the radiation source, and do not hit the detector or the predetermined exposure area on the detector. That is, these X rays do not contribute to the image formed at the detector.

In one embodiment, the movement of the collimator assembly and coordination of the collimator position with at least one of the radiation source positions is achieved through a collimator positioning apparatus 6, as shown in FIG. 1, which comprises an electro-mechanical system 13 and a software program of a system controller which computes the positions on the basis of input signals and generates an output signal for providing the desired movement of the collimator.

The displacement by the collimator positioning apparatus results in different configurations of the collimator assembly. Each configuration corresponds to a specific collimator position. Further, the collimator assembly is configured to displace the collimator in a plurality of collimator positions with respect to the radiation source, each one of the collimator positions corresponding to one of the radiation source positions.

Figure 7:
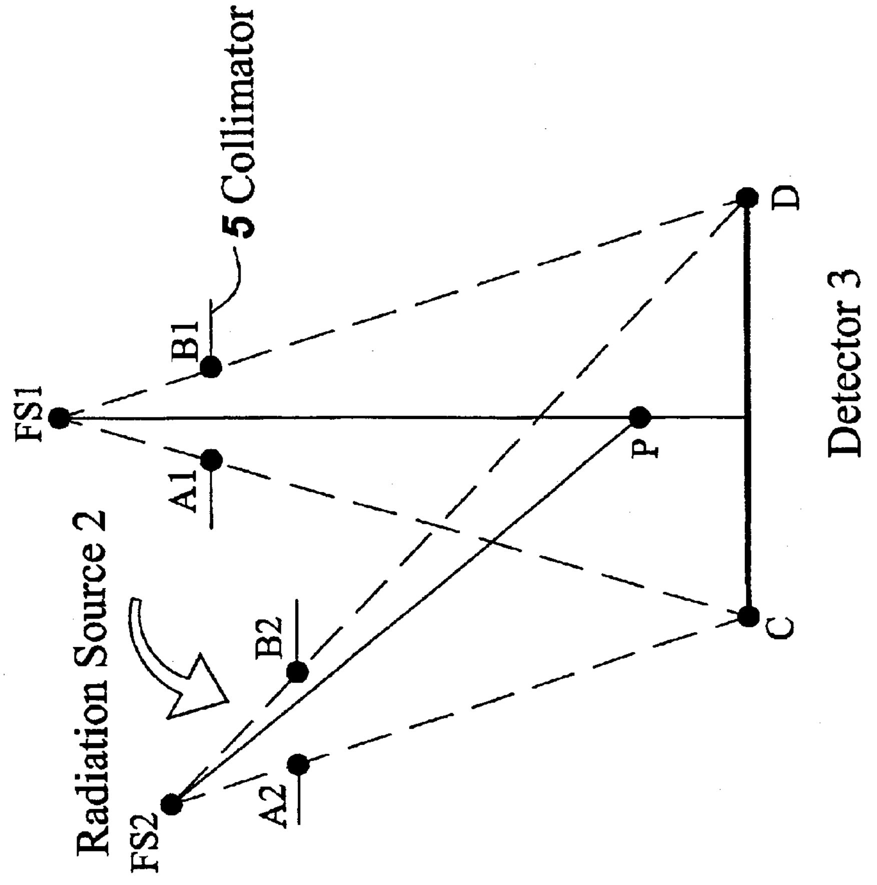
FIG. 7 illustrates one embodiment of the invention wherein projection of the collimator aperture coincides exactly with the active area of the detector.

Typically the collimator positioning apparatus 6 has a displacement mechanism 7. In one embodiment the displacement mechanism comprises a rotational displacement mechanism, for positioning the collimator axially as shown in FIG. 7, that is, at an angle, with respect to the radiation source and the detector to achieve a rotational displacement. In another embodiment, the displacement mechanism comprises a translational displacement mechanism, for positioning the collimator horizontally with respect the radiation source and the detector to achieve a translational displacement. In still another embodiment, the displacement mechanism comprises a multi-axis displacement mechanism, for positioning collimator both axially and horizontally with respect to the radiation source and the detector to achieve multi axis displacement.

The imaging system is typically coupled to a system controller, which includes a software program to calculate the various displacements and positions of the movable elements of the imaging system including the radiation source, the collimator assembly and the collimator. The system controller is programmed to control the collimator positioning apparatus so as to displace the collimator in plurality of collimator positions. In a more specific embodiment, the displacement of the collimator position with respect to the radiation source corresponds to the respective displacement of the radiation source with respect to the detector.

Figure 3:
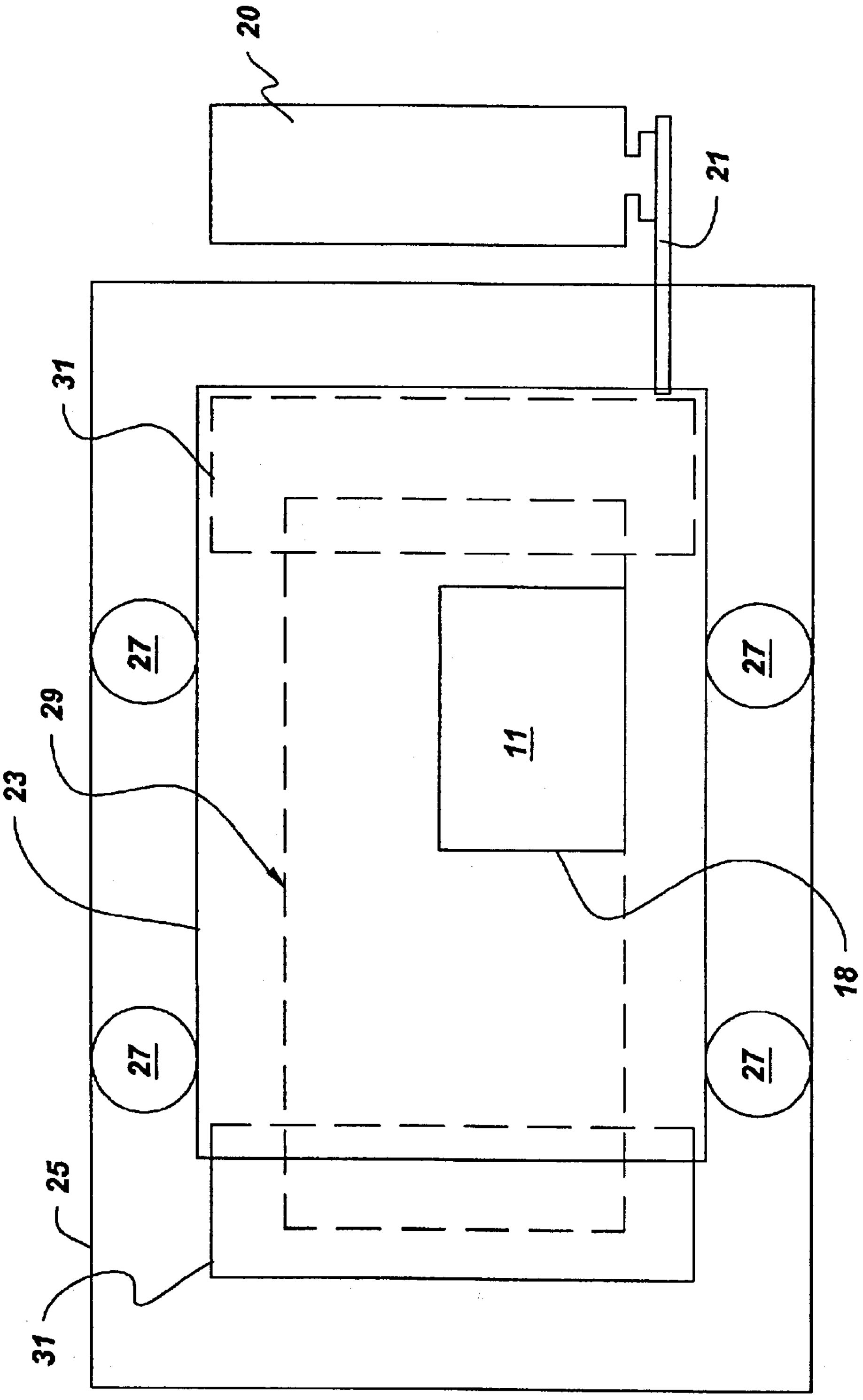
FIG. 3 illustrates a collimator assembly including a collimator in one embodiment of the invention.

In one embodiment, the aperture assembly has a fixed geometry aperture, that is an aperture made of fixed sides 18. In a more specific embodiment, as shown in FIG. 3, the fixed geometry aperture has a rectangular cross-section. In an even more specific embodiment, aperture 11 is positioned within an aperture plate 23 which is movably mounted relative to a base plate 25 via guide wheels 27, drive belt 21, and stepper motor 20. If the base plate opening 29 is sized such that movement of aperture plate 23 potentially exposes X-rays through opening 29, it is useful to mechanically couple sliding plates 31 to aperture plate 23 to prevent such exposure.

Figure 10:
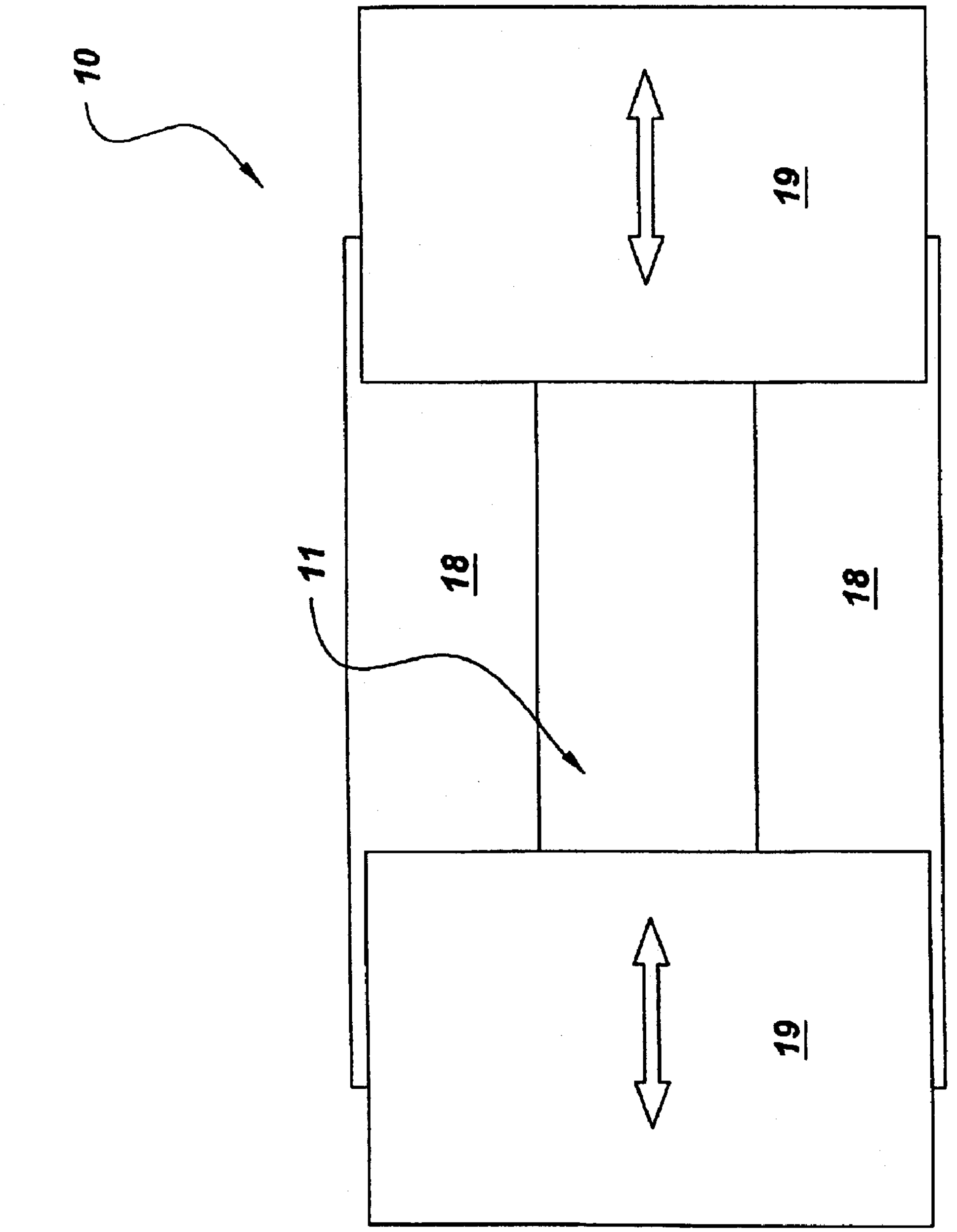
FIG. 10 is a top view of an embodiment of the invention wherein an aperture assembly is configured to provide an adjustable geometry aperture.

In another embodiment, the collimator further comprises an aperture assembly 10, configured to provide an adjustable geometry aperture 11 as shown in FIG. 10. In a more specific embodiment, the aperture assembly has at least one side 19 movable rotationally, translationally, or a combination thereof.

Alternatively or additionally, the aperture assembly comprises a plurality of movable sides 19. In another embodiment the aperture assembly comprises multiple sections, with different boundary shapes that can be independently positioned to form an adjustable geometry aperture. Further in another embodiment the multiple sections can have linear boundaries that can be independently positioned. Another embodiment comprises a plurality of sides movable both rotationally and translationally. The aperture assembly typically comprises a radiation absorbing material such as tungsten or some other high atomic number (greater than about 74, for example) material and is adapted to adjust aperture geometry to limit radiation incident on the detector to the predetermined exposure area.

When the radiation source moves from one position to the next, the aperture is adjusted accordingly. The movement of radiation source and adjustment of aperture are synchronized, that is, their timing is coordinated. Furthermore, at least one of the position and the shape of the aperture during exposure (i.e., at the instant an image is acquired) is coordinated relative to the position of the radiation source, and relative to the position of the detector. The fact that the position of the aperture is appropriately coordinated with the position of source and detector ensures that no radiation spills beyond the edge of the detector (or active area/predetermined exposure area). In one embodiment, synchronization and position coordination are controlled by the stepper motor 20 and drive belt 21 (such as shown in FIG. 3, for example), driven by system controller 15 and a generator 16 (shown in FIG. 1).

The collimator is typically mounted as close to the focal spot as possible, to minimize size and weight and maximize speed of operation. One use of such a collimator assembly is in a mammography system, where the rotation axis of the tube arm is about 22 cm above the face of the detector. In this geometry, the X ray beam is not centered on the detector except for exposures taken at the vertical (0-degree) position.

Figure 4:
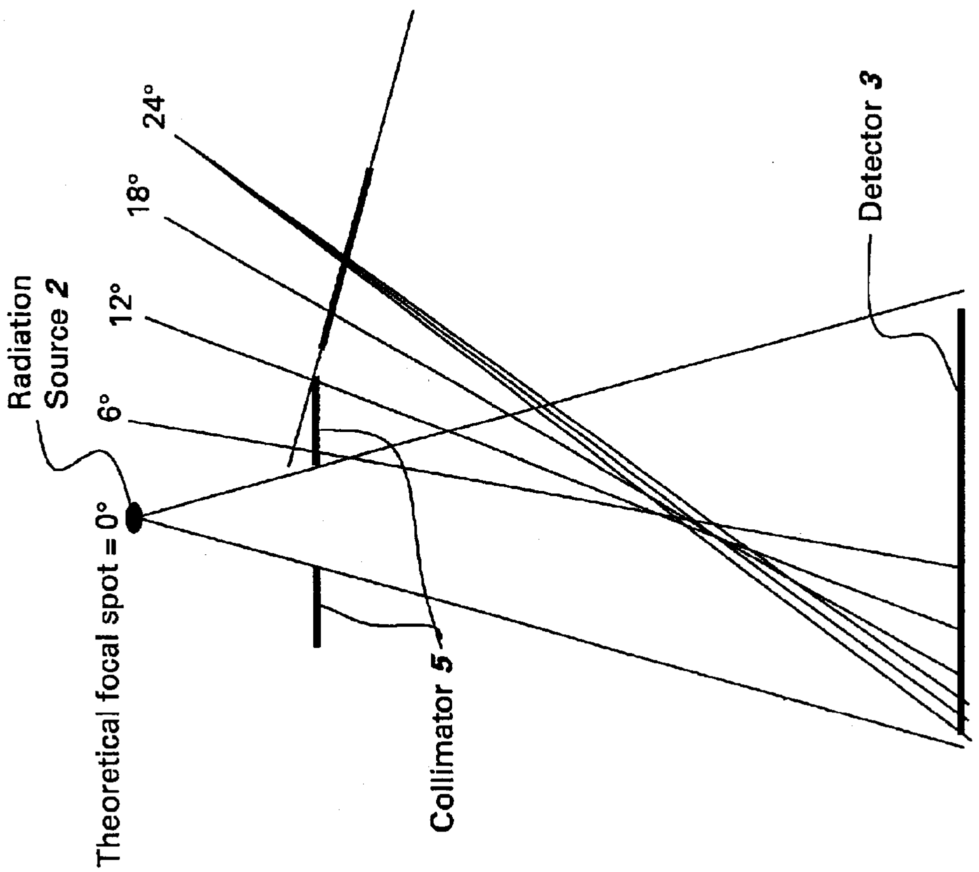
FIG. 4 illustrates use of a traditional collimator in a Mammography system, depicting the different field of views at the detector for different radiation source positions and respective collimator aperture geometry configurations.
Figure 5:
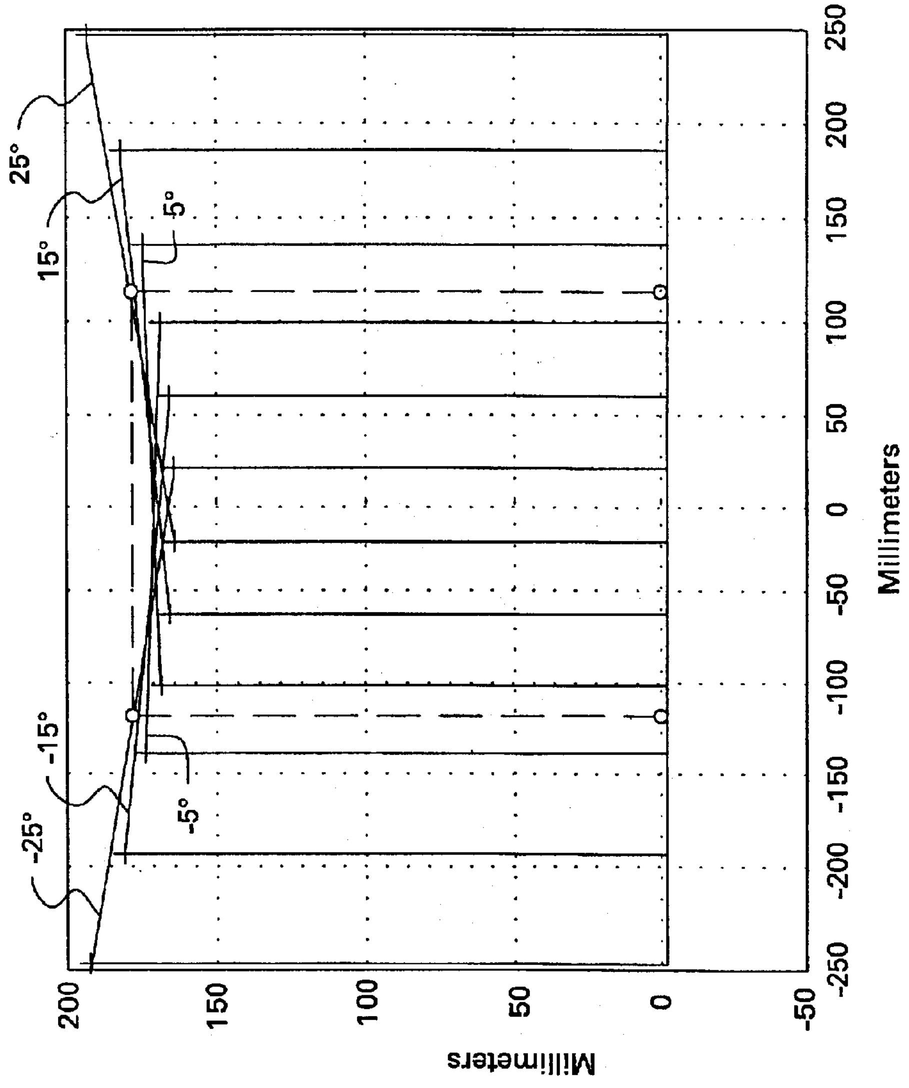
FIG. 5 illustrates the shape of the collimated beam falling onto the detector plane, relative to the detector, for a fixed rectangular aperture, according to one embodiment of the invention corresponding to the system geometry depicted in FIG. 2 and a stationary (i.e., not moving) collimator.
Figure 6:
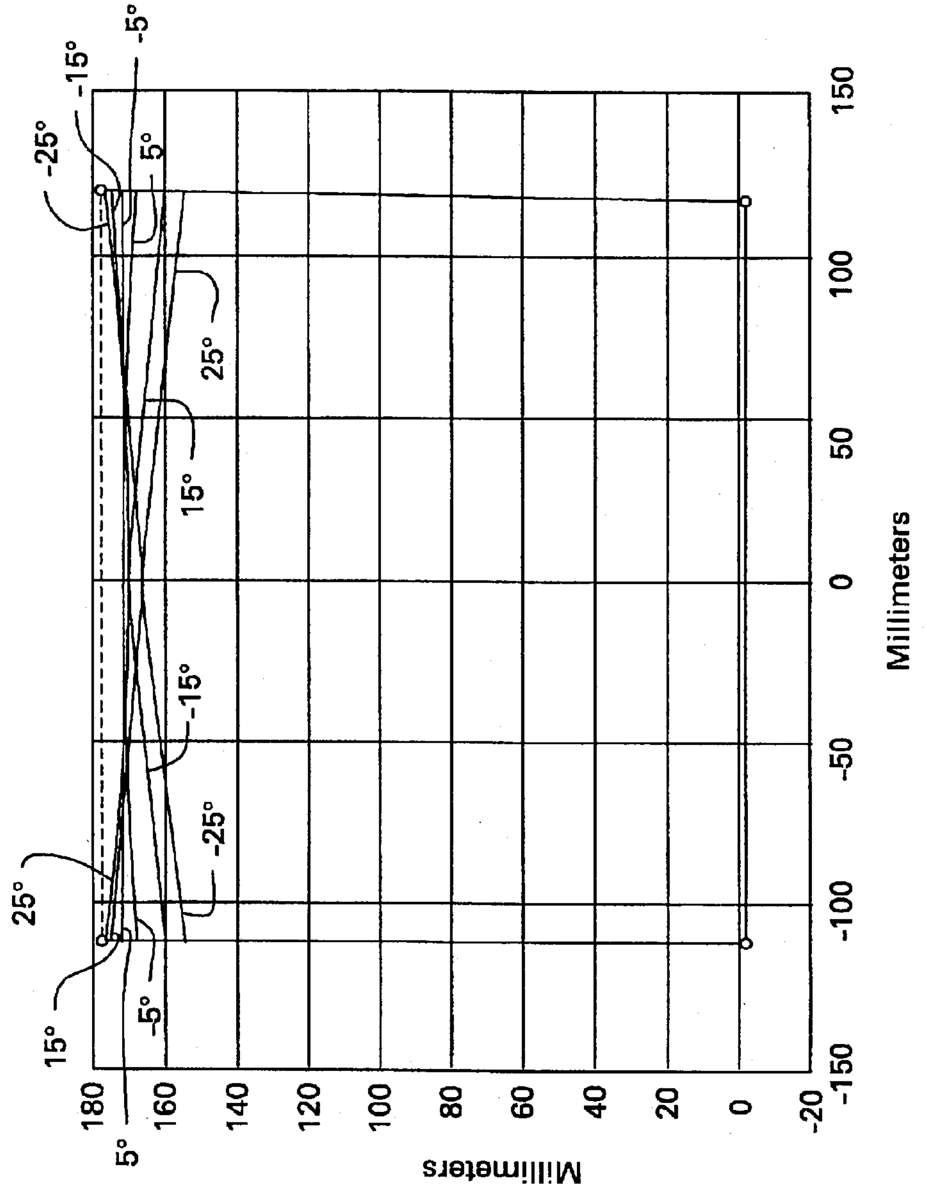
FIG. 6 illustrates the shape of the collimated beam falling onto the detector plane, relative to the detector, for a fixed rectangular aperture, according to another embodiment of the invention corresponding to the system geometry depicted in FIG. 2 for a translatable collimator.

The intersection of the center of the X-ray beam with the image receptor at various angles of tube inclination is shown in FIG. 4. The width of a conventional adjustable collimator aperture, which is symmetric with respect to the center of the beam, has to be decreased with increasing tube inclination angle, in order to avoid any spill beyond the edge of the detector. As shown in FIG. 4, the resulting area of exposure on the detector is very small (about 35 mm in width or smaller, for example) for high tube angles (greater than about 24 degrees, for example) and is not practical. In one embodiment of the present invention one uses a translatable collimator with a fixed rectangular aperture. Using this embodiment, one can achieve almost optimal coverage of the detector, without any spill beyond the edge of the detector. FIGS. 5 and 6 show the shape of the collimated beam falling onto the detector, for a fixed rectangular aperture. FIG. 5 illustrates a stationary (i.e., not moving) collimator, with spill beyond the edge of the detector. FIG. 6 illustrates a translatable collimator, with no spill, and for every angle of inclination of the tube, almost all of the detector surface is irradiated by the beam.

Figure 9:
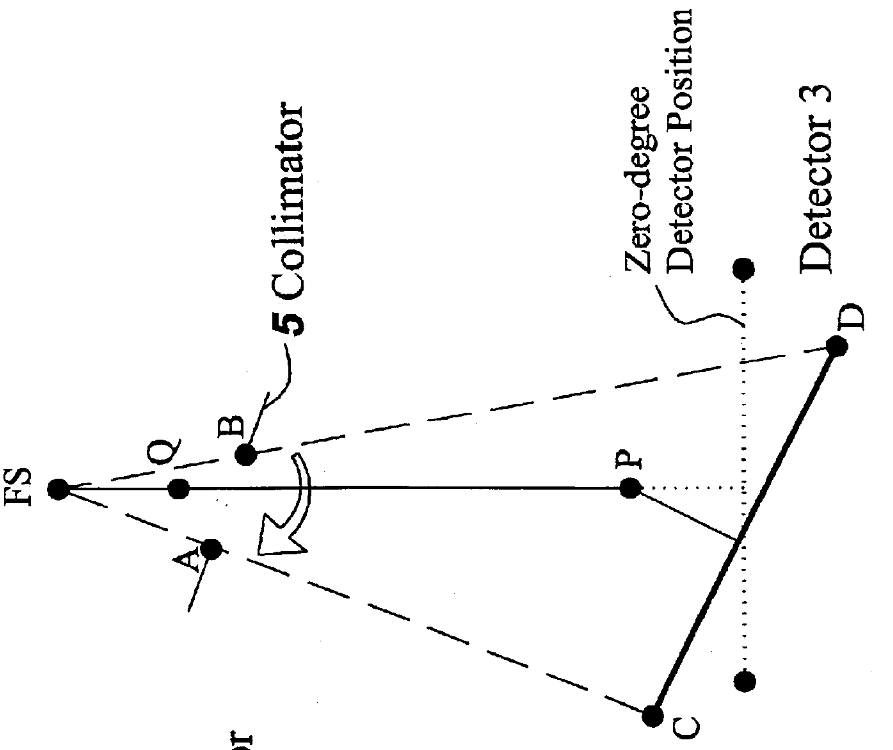
FIG. 9 illustrates another embodiment of the invention where the movement of the radiation source with respect to the detector is the same as the movement of the radiation source with respect to the aperture and shows the geometric relationships with the radiation source rotated at an angle.
Figure 8:
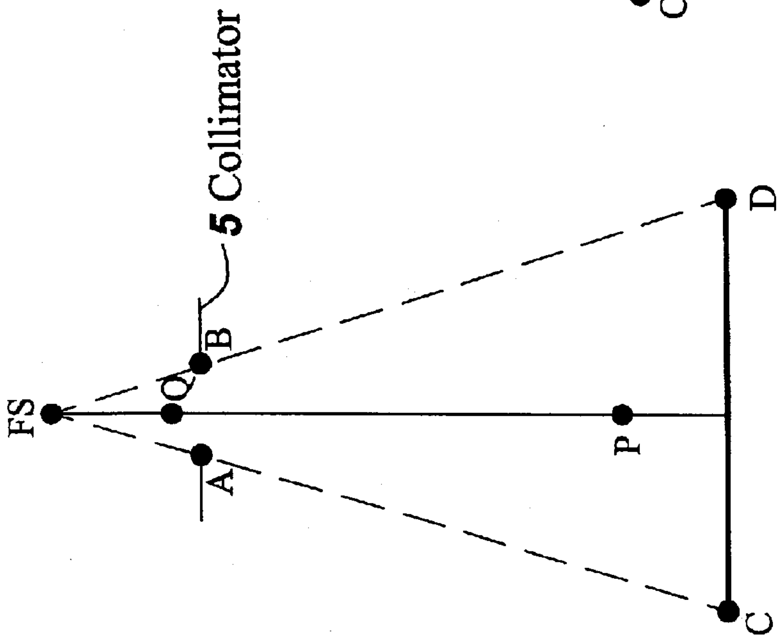
FIG. 8 illustrates one embodiment of the invention where the movement of the radiation source with respect to the detector is the same as the movement of the radiation source with respect to the aperture and shows the geometric relationships for a vertical position of the X Ray source.

In one embodiment of the invention, at least one of the shape of the collimator aperture and the movement of the collimator is controlled such that the relative position of the radiation source with respect to the collimator aperture is the same (meaning identical up to a magnification or scaling factor) as the relative position of the radiation source with respect to the detector. The advantages are that there is no spill of X rays beyond the edge of the active area of the detector and there is no shadow of the collimator falling on the active area of the detector, which results in an optimal field of view. FIG. 7 illustrates the relative positions of radiation source (FS) and the position of the collimator 5 (with an aperture defined by points AB) with respect to the detector 3 (defined at points CD) and a rotation point P. In this embodiment, the generalized pyramid defined by the set of points [FS,C,D ] is a magnified or scaled version of the generalized pyramid defined by the set of points FS,A,B. In one embodiment of the invention the magnification or scaling is kept constant for plurality of radiation source positions. In FIG. 7, the desired scaling is achieved when distance A1B1 equals distance A2B2, and they are both equal to "s" times the distance CD, where "s" is the magnification or scaling factor. In one embodiment, an essentially similar mechanical arrangement, a scaled down version in size by a factor "1/s" as defined earlier is used to move the collimator relative to the radiation source, as is used to move the radiation source relative to the detector. Referring to FIGS. 8 and 9, the geometry of the set of points [FS,A,B,Q] is a magnified or scaled version of the geometry of the points [FS,C,D,P] and rotation of the radiation source around point P corresponds to the rotation of the collimator around point Q to optimally position the collimator. One geometry being a magnified or scaled version of the other geometry means that any point in the first geometry has a corresponding point in the second geometry; further, that the distance between any two points in the first geometry is equal to "s" times the distance between the corresponding points in the second geometry, where "s" is the magnification or scaling factor, and that the line passing through the two points in the first geometry has the same orientation as the line passing through the corresponding two points in the second geometry. FIG. 8 illustrates one embodiment of the invention where the movement of the radiation source with respect to the detector is the same (up to a magnification or scaling factor) as the movement of the radiation source with respect to the aperture and shows the geometric relationships for a vertical position of the X Ray source, and FIG. 9 illustrates another embodiment of the invention where the movement of the radiation source with respect to the detector is the same (up to a magnification or scaling factor) as the movement of the radiation source with respect to the aperture and shows the geometric relationships with the radiation source rotated at an angle. For ease of interpretation, in FIG. 9 the radiation source is drawn in the same position as in FIG. 8, with the radiation detector and the collimator rotated correspondingly.

Another embodiment of the present invention is a method of radiation imaging, which includes positioning of a radiation source in a plurality of radiation source positions, displacing the collimator in a plurality of respective collimator positions such that each collimator position corresponds to a respective one of the radiation source position to collimate and limit the radiation beam emanating from the radiation source to a predetermined exposure area and detecting the radiation beam on a radiation detector.

In another embodiment of the present invention, a radiation imaging system comprises: a movable radiation source; a radiation detector; and a collimator comprising an adjustable geometry aperture assembly configured such that an adjustment of the aperture geometry is synchronized with the movement of said radiation source and coordinated with the radiation source position so as to limit the incident radiation to a predetermined exposure area at said detector. The above described more specific aperture assembly embodiments are also applicable in this embodiment. The adjustable aperture geometry embodiment can be used to obviate the need for changing collimator positions as described above with respect to the displaceable collimator embodiment and may be used independently of or in combination with the displaceable collimator embodiment.

As described above, adjustment of the aperture geometry is synchronized with the movement of said radiation source by coordinating their timing, and the aperture geometry adjustment is further coordinated (i.e., at the instant an image is acquired) relative to the position of the radiation source, and relative to the position of the detector. The fact that the position of the aperture is appropriately coordinated with the position of source and detector ensures that no radiation spills beyond the edge of the detector (or active area / predetermined exposure area). In one embodiment, synchronization and position coordination are controlled by the stepper motor and drive belt mechanism driven by a system controller and a generator.

Another embodiment of the present invention is a method for radiation imaging, which includes moving a radiation source in a plurality of radiation source positions, adjusting an aperture by synchronizing the aperture geometry adjustment with the movement of the radiation source and coordinating at least one of the position and the shape of the aperture with the respective position of the radiation source such that a radiation beam emanating from the radiation source is collimated to limit the incident radiation to a predetermined exposure area and detecting the radiation beam on a radiation detector While only certain features of the invention have been illustrated and described herein, many modifications and changes will occur to those skilled in the art. It is, therefore, to be understood that the appended claims are intended to cover all such modifications and changes as fall within the true spirit of the invention.

what is claimed is:

1. A radiation imaging system comprising:

a movable radiation source configured to be displaced in a plurality of respective radiation source positions;

a radiation detector;

a collimator assembly, said assembly comprising a collimator, said assembly further being configured to displace the collimator in a plurality of respective collimator positions, each of said collimator positions being coordinated with at least one of said radiation source positions such that a radiation beam emanating from said radiation source is collimated to limit radiation incident on said detector to a predetermined exposure area.

2. The imaging system of claim 1 wherein said collimator assembly further comprises a collimator positioning apparatus for displacing said collimator in respective ones of said collimator positions, each of said collimator positions corresponding to a respective spatial relationship with said radiation source and said detector.

3. The imaging system of claim 2 wherein said collimator positioning apparatus further comprises a displacement mechanism comprising: a rotational displacement mechanism adapted to position the collimator axially with respect to the radiation source and the detector.

4. The imaging system of claim 2 wherein said collimator positioning apparatus further comprises a translational displacement mechanism adapted to position the collimator horizontally with respect to the radiation source and the detector.

5. The imaging system of claim 2 wherein said collimator positioning apparatus further comprises a multi-axis displacement mechanism adapted to position the collimator both axially and horizontally with respect to the radiation source and the detector.

6. The imaging system of claim 1, wherein each one of said collimator positions corresponds to exactly one of said radiation source positions.

7. The imaging system of claim 1, wherein said collimator further comprises an aperture assembly, said aperture assembly being configured to provide an adjustable geometry aperture.

8. The imaging system of claim 1, wherein said collimator further comprises an aperture assembly comprising radiation absorbing material and adapted to provide an adjustable geometry aperture to limit radiation incident on said detector to said predetermined exposure area.

9. The imaging system of claim 7, wherein said aperture assembly comprises a plurality of movable sides.

10. The imaging system of claim 7, wherein said aperture assembly comprises at least one movable side.

11. The imaging system of claim 7, wherein said aperture assembly comprises multiple independently positionable sections with different boundary shapes.

12. The imaging system of claim 11, wherein said multiple sections have linear boundaries.

13. The imaging system of claim 10, wherein said plurality of sides comprise rotationally and translationally movable sides.

14. The imaging system of claim 1, wherein said collimator further comprises an aperture of fixed geometry.

15. The imaging system of claim 14, wherein said fixed geometry aperture has a rectangular cross-section.

16. The imaging system of claim 15, wherein movement of said radiation source relative to said detector is the same as the movement of said radiation source relative to said aperture.

17. A method for radiation imaging, comprising:

positioning a radiation source in a plurality of respective radiation source positions;

displacing a collimator in a plurality of respective collimator positions, each of said collimator positions corresponding to a respective one of said radiation source positions such that a radiation beam emanating from said radiation source is collimated to limit the incident radiation to a predetermined exposure area; and detecting the radiation beam on a radiation detector.

18. The method of claim 17, wherein displacing said collimator comprises: displacing said collimator such that each of said collimator positions corresponds to a respective spatial relationship with said radiation source and said radiation detector.

19. The method of claim 18, wherein displacing said collimator comprises positioning the collimator axially with respect to the radiation source and the detector.

20. The method of claim 18, wherein displacing said collimator comprises positioning the collimator horizontally with respect to the radiation source and the detector.

21. The method of claim 18, wherein displacing said collimator comprises positioning the collimator both axially and horizontally with respect to the radiation source and the detector.

22. The method of claim 17, wherein displacing said collimator in said plurality of collimator positions is done such that each one of said collimator positions corresponds to exactly one of said radiation source positions.

23. The method of claim 17, wherein displacing said collimator further comprises adjusting the geometry of an aperture.

24. The method of claim 23, wherein adjusting the geometry of the aperture comprises moving a plurality of sides of an aperture assembly of said collimator.

25. The method of claim 23, wherein adjusting the geometry of the aperture comprises moving of at least one side of an aperture assembly of said-collimator.

26. The method of claim 17, wherein displacing said collimator further comprises adjusting the geometry of an aperture for limiting radiation incident on said detector to said predetermined exposure area.

27. The method of claim 21, wherein the collimator comprises an aperture, and wherein positioning the radiation source and displacing the collimator are performed to provide movement of said radiation source relative to said detector that is the same as movement of said radiation source relative to said aperture.

28. A radiation imaging system comprising:

a movable radiation source adapted to be disposed in a plurality of respective radiation source positions;

a radiation detector;

a collimator assembly, said assembly comprising a collimator comprising an aperture assembly configured to provide an aperture and a collimator positioning apparatus for displacing said collimator in a plurality of respective collimator positions, each of said collimator positions being coordinated with at least one of said radiation source positions such that a radiation beam emanating from said radiation source is collimated through the aperture to limit radiation incident on said detector to a predetermined exposure area.

29. The imaging system of claim 28, wherein each of said collimator positions corresponds to a respective spatial relationship with said radiation source and said radiation detector.

30. The imaging system of claim 28, wherein each one of said collimator positions corresponds to exactly one of said radiation source positions.

31. The imaging system of claim 28, wherein said aperture assembly is configured to provide an adjustable geometry aperture.

32. The imaging system of claim 31, wherein said aperture assembly comprises a plurality of movable sides.

33. The imaging system of claim 31, wherein said aperture assembly comprises at least one movable side.

34. The imaging system of claim 28, wherein said aperture assembly is configured to provide an aperture of fixed geometry.

35. The imaging system of claim 34, wherein the aperture of fixed geometry has a rectangular cross-section.

* * * * *

UNITED STATES PATENT AND TRADEMARK OFFICE

CERTIFICATE OF CORRECTION

PATENT NO. : 6,647,092 B2
DATED : November 11, 2003
INVENTOR(S) : Jeffrey W. Eberhard et al.

It is certified that error appears in the above-identified patent and that said Letters Patent is hereby corrected as shown below:

Column 1,
Line 5, delete "DAMD17988109" and insert -- DAMD17-98-1-8309 -- therefor.

Signed and Sealed this

Fifteenth Day of June, 2004

JON W. DUDAS
*Acting Director of the United States Patent and Trademark Office*